US010048278B2

(12) United States Patent
Cox et al.

(10) Patent No.: US 10,048,278 B2
(45) Date of Patent: *Aug. 14, 2018

(54) SCREENING FOR NEUROTOXIC AMINO ACID ASSOCIATED WITH NEUROLOGICAL DISORDERS

(71) Applicant: THE INSTITUTE FOR ETHNOMEDICINE, Provo, UT (US)

(72) Inventors: Paul Alan Cox, Provo, UT (US); Sandra Banack, Fullerton, CA (US); Susan Murch, Cambridge (CA)

(73) Assignee: THE INSTITUTE FOR ETHNOMEDICINE, Jackson, WY (US)

(*) Notice: Subject to any disclaimer, the term of this patent is extended or adjusted under 35 U.S.C. 154(b) by 0 days.

This patent is subject to a terminal disclaimer.

(21) Appl. No.: 14/033,150

(22) Filed: Sep. 20, 2013

(65) Prior Publication Data

US 2014/0080140 A1  Mar. 20, 2014

Related U.S. Application Data

(60) Continuation of application No. 13/015,288, filed on Jan. 27, 2011, now Pat. No. 8,541,184, which is a continuation of application No. 11/837,899, filed on Aug. 13, 2007, now Pat. No. 7,901,895, which is a division of application No. 10/731,411, filed on Dec. 8, 2003, now Pat. No. 7,256,002.

(60) Provisional application No. 60/494,686, filed on Aug. 13, 2003.

(51) Int. Cl.
*G01N 33/68* (2006.01)
*G01N 33/94* (2006.01)

(52) U.S. Cl.
CPC ..... *G01N 33/6896* (2013.01); *G01N 33/6812* (2013.01); *G01N 33/94* (2013.01); *G01N 2410/00* (2013.01); *G01N 2550/00* (2013.01); *G01N 2800/28* (2013.01); *Y02A 50/57* (2018.01)

(58) Field of Classification Search
CPC ........... G01N 33/6812; G01N 33/6896; G01N 2800/28; G01N 2410/00
See application file for complete search history.

(56) References Cited

U.S. PATENT DOCUMENTS 6,043,283 A   3/2000  Giulian

FOREIGN PATENT DOCUMENTS

WO   WO 02/37122 A2   5/2002

OTHER PUBLICATIONS

Alberts et al. *Molecular Biology of the Cell.* 3rd ed. New York: Garland Publishing; 1994:49, 56, and 132.
Armon, C. Western Pacific ALS/PDC and flying foxes. *Neurology* Aug. 2003; 61:291-292.
Banack, 2002. Oral Session #89, Biodiversity and Ecosystem Function III, Ecological Society of America Annual Meeting. Presented Thursday Aug. 8, 2002.
Banack et al. Biomagnification of cycad neurotoxins in flying foxes, Implications for ALS-PDC in Guam. *Neurology* Aug. 12, 2003; 61(3):387-389.
Banack et al. Distribution of the neurotoxic nonprotein amino acid BMAA in Cycas micronesica. *Botanical Journal of the Linnean Society* 2003; 143:165-168.
Bjartmar et al. Axonal loss in the pathology of MS: consequences for understanding the progressive phase of the disease. *J. Neurol Sci* 2003; 206:165-171.
Brenner et al. Cycads: evolutionary innovations and the role of plant-derived neurotoxins. *Trends in Plant Science* Sep. 2003; 8(9):446-452.
Brownson et al. The cycad neurotoxic amino acid, β-N-methylamino-$_L$-alanine (BMAA), elevates intracellular calcium levels in dissociated rat brain cells. *Journal of Ethnopharmacology* 2002; 82:159-167.
Cassel et al. Demography and Epidemiology of Age-Associated Neuronal Impairment. In: PR HOF and CV Mobbs, eds. *Functional Neurobiology of Aging* San Diego: Academic Press. 2000:31-50.
Charlton et al. Quantification of the Neurotoxin 2-Amino-3-(Methylamino)-propanoic acid (BMAA) in Cycadales. *Phytochemistry* 1992; 31(10):3429-3432.
Chen et al. Cycad neurotoxin, consumption of flying foxes, and ALS/PDC disease in Guam and author reply. *Neurology* Nov. 26, 2002; 59 (10):1664-1665.
Cluskey et al. Mechanisms of neurodegeneration in amyotrophic lateral sclerosis. *Mol Pathol* 2001; 54:386-392.
Cox et al. Biomagnification of cyanobacterial neurotoxins and neurodegenerative disease among the Chamorro people of Guam. *PNAS(USA)* Nov. 11, 2003; 100(23):13380-13383.
Cox et al. Cycad neurotoxins, consumption of flying foxes, and ALS-PDC disease in Guam. *Neurology* Mar. 26, 2002; 58(6):956-959.
Deumens et al. Modeling Parkinson's Disease in Rats: An Evaluation of 6-OHDA Lesions of the Nigrostriatal Pathway. *Experimental Neurology* 2002; 175:303-317.
Duncan et al. 2-Amino-3-(methylamino) propanoic acid (BMAA) Bioavailability in the Primate. *Neurobiology of Aging* 1992; 13(2):333-337.

(Continued)

*Primary Examiner* — Robert C Hayes
(74) *Attorney, Agent, or Firm* — Pillsbury Winthrop Shaw Pittmann LLP

(57) ABSTRACT

Methods for screening for neurological disorders are disclosed. Specifically, methods are disclosed for screening for neurological disorders in a subject by analyzing a tissue sample obtained from the subject for the presence of elevated levels of neurotoxic amino acids or neurotoxic derivatives thereof associated with neurological disorders. In particular, methods are disclosed for diagnosing a neurological disorder in a subject, or predicting the likelihood of developing a neurological disorder in a subject, by determining the levels of β-N-methylamino-L-alanine (BMAA) in a tissue sample obtained from the subject. Methods for screening for environmental factors associated with neurological disorders are disclosed. Methods for inhibiting, treating or preventing neurological disorders are disclosed.

11 Claims, 1 Drawing Sheet

(56) References Cited

OTHER PUBLICATIONS

Duncan et al. 2-Amino-3-(methylamino)-propanoic acid (BMAA) in cycad flour: An unlikely cause of amyotrophic lateral sclerosis and parkinsonism-dementia of Guam. *Neurology* May 1990; 40(5):767-772.
Duncan et al. 2-Amino-3-(methylamino)-propanoic acid (BMAA) Pharmacokinetics and Blood-Brain Barrier Permeability in the Rat. *The Journal of Pharmacology and Experimental Therapeutics* 1991; 258(1):27-35.
Duncan et al. Quantification of the Putative Neurotoxin 2-Amino-3-(methylamino)propanoic Acid (BMAA) in Cycadales: Analysis of the Seeds of Some Members of the Family Cycadaceae. *Journal of Analytical Toxicology* May/Jun. 1989; 13(3):169-175.
Duncan et al. Zinc, a Neurotoxin to Cultured Neurons, Contaminates Cycad Flour Prepared by Traditional Guamanian Methods. *The Journal of Neuroscience* Apr. 1992; 12(4):1523-1537.
Ellison et al. A Postmortem Study of Amino Acid Neurotransmitters in Alzheimer's Disease. *Ann Neurol* 1986; 20:616-621.
Forman et al. Tau and α-Synuclein Pathology in Amygdala of Parkinsonism-Dementia Complex Patients of Guam. *American Journal of Pathology* May 2002; 160(5):1725-1731.
Furey et al. The first identification of the rare cyanobacterial toxin, homoanatoxin-a, in Ireland. *Toxicon* 2003; 41:297-303.
Giannakopoulos et al. Types of Age-Related Brain Lesions and Relationship to Neuropathologic Diagnostic Systems of Alzheimer's Disease. In: PR HOF and CV Mobbs, eds. *Functional Neurobiology of Aging*. San Diego:Academic Press; 2000: 65-76.
Haider et al. Cyanobacterial toxins: a growing environmental concern. *Chemosphere* 2003; 52:1-21.
Hampton, Food Chain of Evidence Points to Brain Toxin. *JAMA* Dec. 3, 2003; 290(21):2788-2789.
Harvey et al. Memory Changes with Aging and Dementia, in: PR HOF and CV Mobbs, eds. *Functional Neurobiology of Aging*. San Diego:Academic Press; 2000:53-63.
Hoffner et al. Protein aggregation in Huntington's disease. *Biochimie* 84 (2002) pp. 273-278.
Kandel et al. *Principles of Neural Science*, $3^{rd}$ ed. New York: Elsevier; 1991:980.
Kisby et al. Content of the neurotoxins cycasin (methylazoxymethanol β-$_D$-glucoside) and BMAA (β-N-methylamino-$_L$-alanine) in cycad flour prepared by Guam Chamorros. *Neurology* 1992; 42(7):1336-1340.
Kisby et al. Cycasin and BMAA: Candidate Neurotoxins for Western Pacific Amyotrophic Lateral Sclerosis/Parkinsonism-Dementia Complex. *Neurodegeneration* 1992; 1(1):73-82.
Kisby et al. Determination of β-N-methylamino-$_L$-alanine (BMAA) in plant (*Cycas circinalis* L.) and animal tissue by precolumn derivatization with 9-fluorenylmethyl chloroformate (FMOC) and reversed-phase high-performance liquid chromatography. *Journal of Neuroscience Methods* 1988; 26(1):45-54.
Lewin, R., Environmental Hypothesis for Brain Diseases Strengthened by New Data. *Science* 1987; 237:483-484.
Martinez, et al. Amino acid concentrations in cerebrospinal fluid and serum in Alzheimer's disease and vascular dementia. *J Neural Transm Park Dis Dement Sect* 1993; 6:1-9.
Monson et al. Conservation Implications of Chamorro Consumption of Flying Foxes as a Possible Cause of Amyotrophic Lateral Sclerosis-Parkinsonism Dementia Complex in Guam. *Conservation Biology* Jun. 2003; 17(3):678-686.
Myers et al. Neuroactive Carbamate Adducts of β-N-Methylamino-$_L$-alanine and Ethylenediamine. *J Biol Chem* Jun. 1990; 265(18):10193-10195.
Oh et al. Screening for Non-Protein Amino Acids in Seeds of the Guam Cycad, *Cycas circinalis*, by an Improved GC-MS Method. *Planta Med* 1995; 61(1):66-70.
Pai et al. Billionfold difference in the toxic potencies of two excitatory plant amino acids, L-BOAA and L-BMAA: biochemical morphological studies using mouse brain slices. *Neuroscience Research* 1993; 17:241-248.
Pan et al. Identification of nonprotein amino acids from cycad seeds as N-ethoxycarbonyl ethyl ester derivatives by positive chemical-ionization gas chromatography-mass spectrometry. *Journal of Chromatography A* 1997; 787:288-294.
Perry et al. Amyotrophic Lateral Sclerosis: Amino Acid Levels in Plasma and Cerebrospinal Fluid. *Ann Neurol* 1990:28:12-17.
Schmidt et al. Amyloid plaques in Guam amyotrophic lateral sclerosis/parkinsonism-dementia complex contain species of Aβ similar to those found in the amyloid plaques of Alzheimer's disease and pathological aging. *Acta Neuropathol* 1998; 95:117-122.
Slides from presentation in Honolulu, Hawaii, Dec. 9, 2002, entitled: Island Peoples and Human Health: An Ethnobotanical Approach.
Slides from presentation in Stockholm, Sweden, Jun. 2003, entitled: Biomagnification of Neurotoxins and ALS-PDC in Guam.
Slides from presentation to the Plant Biotechnology and Molecular Biology Program, Colorado State University, Fort Collins, CO, Mar. 2003, entitled: New Drugs from Old Plants.
Slides from presentation to the Trustees of the Edinburgh Botanical Garden in Edinburgh, Scotland, Jun. 2003, entitled: Botanic Gardens and Medicine.
Spencer et al. Guam Amyotrophic Lateral Sclerosis-Parkinsonism-Dementia Linked to a Plant Excitant Neurotoxin, *Science* 1987; 237:517-522.
Vecsei et al. Neurotoxins and Neurodegenerative Disorders. *NeuroToxicology* 1998; 19(4-5):511-514.
Wang et al. Quantitative Analysis of Low Molecular Weight Polar Compounds by Continuous Flow Liquid Secondary Ion Tandem Mass Spectrometry. *Analytical Chemistry* 1989: 61(9):1013-101.

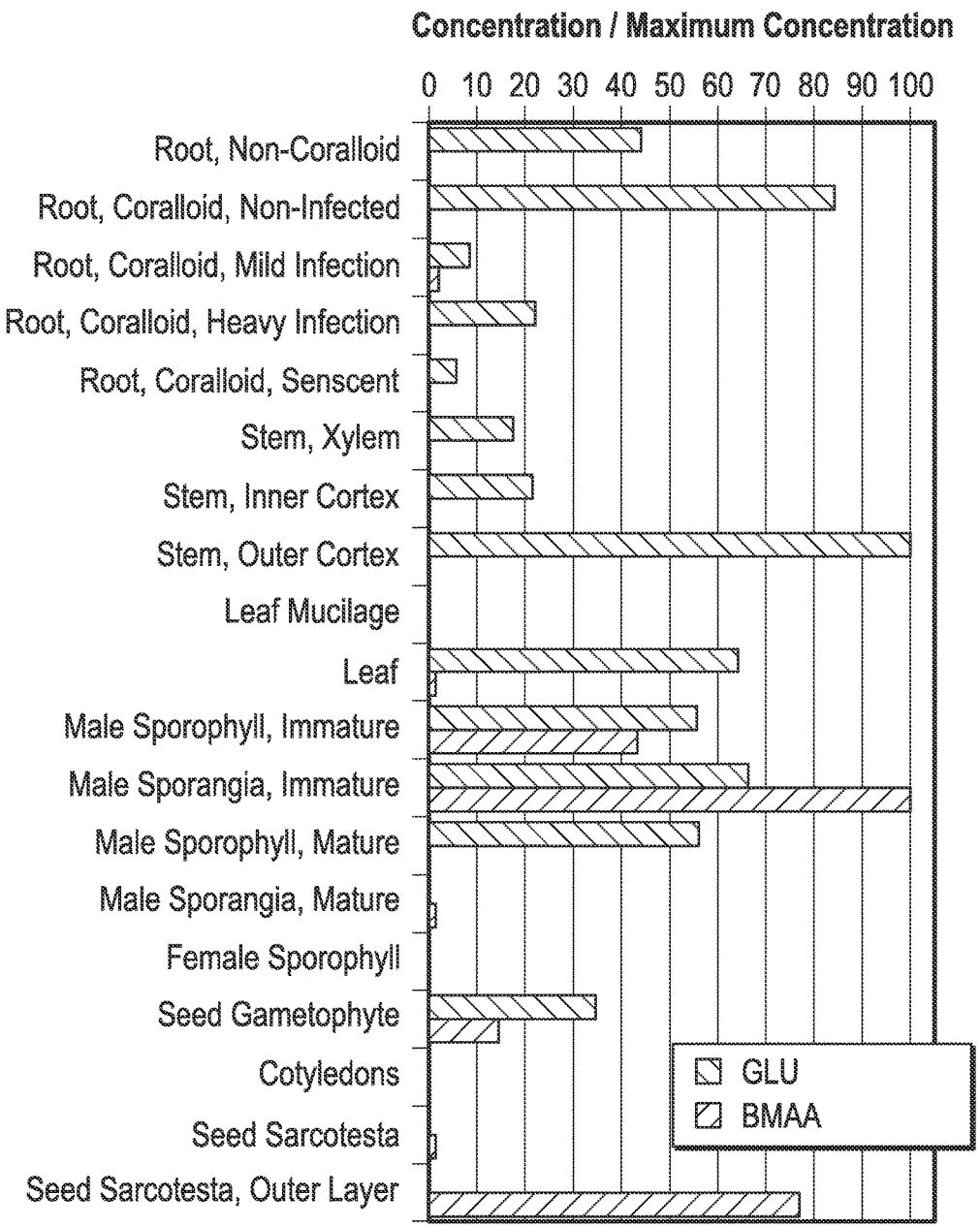

SCREENING FOR NEUROTOXIC AMINO ACID ASSOCIATED WITH NEUROLOGICAL DISORDERS

RELATED APPLICATIONS

This application is a continuation of U.S. patent application Ser. No. 13/015,288, filed Jan. 27, 2011, now allowed, which is a continuation of U.S. patent application Ser. No. 11/837,899, filed Aug. 13, 2007, now U.S. Pat. No. 7,901,895, which is a divisional of U.S. patent application Ser. No. 10/731,411, filed Dec. 8, 2003, now U.S. Pat. No. 7,256,002, which claims the benefit of U.S. Provisional Patent Application No. 60/494,686, filed Aug. 13, 2003 all of which applications are incorporated herein by reference in their entirety.

FIELD OF THE INVENTION

The present invention relates to screening for neurological disorders. Specifically, the invention relates to screening for neurological disorders in a subject by analyzing a tissue sample from the subject to determine the presence of neurotoxic amino acids or neurotoxic derivatives thereof associated with neurological disorders. In particular, the present invention relates to methods for diagnosing a neurological disorder in a subject, or predicting the likelihood of developing a neurological disorder in a subject, by determining the levels of β-N-methylamino-L-alanine (BMAA) or a neurotoxic derivative thereof, in a tissue sample obtained from the subject. Further, the invention relates to screening environmental samples for a neurotoxic amino acid or neurotoxic derivative thereof associated with neurological disorders. Further, the invention relates to inhibiting neurological disorders.

BACKGROUND OF THE INVENTION

A unique neurological disease initially identified among the Chamorro people of Guam by Kurland and Mulder (1954) is characterized by a combination of symptoms including stooped posture, a blank expressionless face, dementia, slow shuffling movement, a resting tremor that stops upon deliberate action, slow movements, and muscle atrophy that results in muscles dipping down in the hand. In some clinical manifestations, patients have clinical symptoms indistinguishable from amyotrophic lateral sclerosis (ALS). Other patients have Parkinsonism features combined with dementia (Parkinsonism Dementia Complex, PDC). In still others, only dementia is observed. Some patients also have both ALS and PDC. Neuropathologically, all clinical forms of the disease result in a specific feature, neurofibrillary tangles, found in the cortex and in the spinal cord. Because the disease has aspects that resemble amyotrophic lateral sclerosis (ALS), Parkinson's disease (PD) and Alzheimer's disease (AD), this disease is known as amyotrophic lateral sclerosis-Parkinsonism dementia complex of Guam (ALS-PDC) and is also known as lytico-bodig.

SUMMARY OF THE INVENTION

The present invention provides methods of screening a subject having or at risk of having a neurological disorder by analyzing a tissue sample from the subject to determine the presence of a neurotoxic amino acid, or neurotoxic derivative thereof, associated with the neurological disorder. The neurotoxic amino acid or neurotoxic derivative thereof can be a glutamate receptor agonist such as β-N-methylamino-L-alanine (BMAA), or β-N-oxalyl-amino-L-alanine (BOAA). In a tissue sample, protein-bound neurotoxic amino acid or neurotoxic derivative thereof can be analyzed, free (unbound) neurotoxic amino acid or neurotoxic derivative thereof can be analyzed, or both protein-bound and free neurotoxic amino acid or neurotoxic derivative thereof can be analyzed in a sample. In a tissue sample, protein-bound BMAA, free BMAA, or both protein-bound BMAA and free BMAA can be analyzed. The subject may have symptoms of a neurological disorder, or may be asymptomatic for a neurological disorder, or may have been identified as being at risk for developing a neurological disorder. The neurotoxic derivative may be any derivative having neurotoxic activity, such as a carbamate adduct or metabolite of the neurotoxic amino acid.

The present invention provides methods of screening a subject having or at risk of having a neurological disorder by analyzing a tissue sample from the subject to determine the presence of a neurotoxic amino acid or neurotoxic derivative thereof associated with the neurological disorder, wherein the presence of a detectable level of a neurotoxic amino acid or neurotoxic derivative thereof indicates a neurological disorder. Methods of the invention can be used to detect neurological disorders including a neurofibrillary tangle disorder (NFT disorder) such as amyotrophic lateral sclerosis-Parkinsonism dementia complex (ALS-PDC), Alzheimer's disease, or progressive supranuclear palsy (PSP), a movement disorder such as Parkinson's disease, or a motor neuron disease such as amyotrophic lateral sclerosis (ALS).

The present invention provides methods of screening a subject having or at risk of having a neurological disorder by analyzing a tissue sample from the subject to determine the presence of a neurotoxic amino acid or neurotoxic derivative thereof associated with the neurological disorder, wherein the methods can be used to predict the likelihood of developing a neurological disease, and/or to predict the latency period prior to onset of the neurological disorder, and/or to predict the severity of the neurological disorder. Methods of the present invention can be practiced using tissue samples including, but not limited to, neurological tissue or non-neurological tissue. Neurological tissue can be associated with the central nervous system (CNS), including brain tissue or cerebral-spinal fluid (CSF), or may be associated with the peripheral nervous system (PNS). Non-neurological tissue can be keratinous tissue including but not limited to, hair, skin, nail, including fingernail or toenail, feather, claw, hoof, or horn. Non-neurological tissue can be non-keratinous tissue including but not limited to, bood, serum, saliva, or urine.

The present invention provides methods for screening an environmental sample to determine if the environmental sample is associated with a neurological disorder, by analyzing the environmental sample to determine the presence of a neurotoxic amino acid or neurotoxic derivative thereof associated with the neurological disorder. The neurotoxic amino acid or neurotoxic derivative thereof can be a glutamate receptor agonist such as a methylated alanine, in particular, BMAA. Suitable environmental samples include water and/or food items or sources.

The present invention provides methods for screening an environmental sample to determine if the sample is associated with a neurological disorder, by detecting neurotoxic amino acid or neurotoxic derivative thereof producing cyanobacteria in the environmental sample. The neurotoxic amino acid or neurotoxic derivative thereof can be a glutamate receptor agonist such as a methylated alanine, in particular, BMAA. Methods of the invention are suitable for detecting cyanobacteria producing the neurotoxic amino acid or neurotoxic derivative thereof, including cyanobacteria of the genus *Nostoc* and/or *Anabena*. Suitable environmental samples include water and/or food items or sources.

The present invention provides methods for inhibiting a neurological disorder in a subject by reducing levels of a neurotoxic amino acid or neurotoxic derivative thereof associated with the neurological disorder, in particular by releasing the neurotoxic amino acid or neurotoxic derivative thereof from an endogenous reservoir. The neurotoxic amino acid or neurotoxic derivative thereof can be a glutamate receptor agonist such as a methylated alanine, in particular, BMAA.

The present invention provides methods inhibiting a neurological disorder in a subject by increasing the cellular concentration of a neuroprotectant compound that blocks interaction of a neurotoxic amino acid or neurotoxic derivative thereof associated with the neurological disorder with a target molecule. The neurotoxic amino acid or neurotoxic derivative thereof can be a glutamate receptor agonist such as a methylated alanine, in particular, BMAA. The neuroprotectant compound can be glutamic acid. An agent that binds or chelates the neurotoxic amino acid or neurotoxic derivative thereof, can be included.

The present invention further provides kits for screening a subject having or at risk of having a neurological disorder, wherein the kits include a means for obtaining a tissue sample from the subject and a means for analyzing the tissue sample to determine the presence of a neurotoxic amino acid or neurotoxic derivative thereof associated with the neurological disorder. The kit may include means for determining the presence of a glutamate receptor agonist such as a methylated alanine, in particular BMAA. The kit may include means for analyzing protein-bound BMAA, free BMAA, or both protein-bound BMAA and free BMAA in the sample. The kit may include means for obtaining and analyzing a plurality of tissue samples from the subject. The tissue samples may include a sample of a tissue in which a neurotoxic amino acid or neurotoxic derivative thereof is known to accumulate and a sample of a tissue in which neurotoxic amino acid or neurotoxic derivative thereof is known to not accumulate. The tissue samples may include a sample of at least two distinct tissues in which a neurotoxic amino acid or neurotoxic derivative thereof is known to accumulate. The kit may include means for performing repeated screening of the subject.

BRIEF DESCRIPTION OF DRAWINGS

FIG. 1 shows concentrations of BMAA and glutamic acid (GLU) in *Cycas micronesia* Hill, normalized by dividing the maximum concentration of each amino acid, which permits a comparison of relative abundance throughout the plant; values below 9 µg/g cannot be seen in this figure as these values are too small relative to the maximum concentration.

Table 1 shows BMAA and GLU concentrations in various tissues of *Cycas micronesia* Hill; concentrations are expressed as µg/g.

Table 2 shows BMAA concentrations in samples of cycad tissues, cyad flour, and flying fox tissues.

Table 3 shows levels of free and protein-associated BMAA in tissue samples from the superior frontal gyrus of patients from Chamorro and Canadian populations.

DETAILED DESCRIPTION OF THE INVENTION

The present disclosure provides methods for screening for neurological disorders. Methods as provided herein can be used to diagnose or predict neurological disorders in a subject, to screen for environmental factors associated with neurological disorders, and to inhibit neurological disorders in a subject.

The present invention provides methods for screening a subject for neurological disorders by analyzing a tissue sample from the subject to determine the presence of a neurotoxic amino acid or neurotoxic derivative thereof associated with the neurological disorder. The present invention further provides methods for screening environmental samples to determine the presence of a neurotoxic amino acid or neurotoxic derivative thereof associated with neurological disorders. The phrase "to determine the presence of a neurotoxic amino acid or neurotoxic derivative thereof" or "determining the presence of a neurotoxic amino acid or neurotoxic derivative thereof" or a similar phrase, includes not only determining the presence or absence of detectable levels of a neurotoxic amino acid or neurotoxic derivative thereof, but also includes quantifying the levels of a neurotoxic amino acid or neurotoxic derivative thereof detected in a sample. Thus, in a particular embodiment, "determining the presence of a neurotoxic amino acid or neurotoxic derivative thereof" in a sample can include determining the level of the neurotoxic amino acid or neurotoxic derivative thereof and can further include determining whether the level of neurotoxic amino acid or neurotoxic derivative thereof in the sample is elevated or decreased in comparison with the levels detected in other samples.

Screening includes but is not limited to, diagnosing or predicting neurological disorders in a subject by analyzing a tissue sample from the subject. Screening may be carried out on a subject having a neurological disorder, or may be carried out on a subject at risk of having a neurological disorder, or may be carried out on a subject having no known risk of having a neurological disorder. Screening further includes analyzing environmental samples to determine actual or potential exposure of a subject to a neurotoxic amino acid or neurotoxic derivative thereof associated with a neurological disorder.

As provided herein, neurotoxic amino acids or neurotoxic derivatives thereof associated with neurological disorders include, but are not limited to, non-protein amino acids, excitatory amino acids, amino acid analogs, amino acid metabolites, carbamate adducts of amino acids, and conjugates of amino acids. In one embodiment, one or more neurological disorders can be screened for in a subject by determining the presence of β-N-methylamino-L-alanine (BMAA) in a sample of tissue obtained from the subject. In another embodiment, one or more neurological disorders can be screened for by determining the presence of (S)-2-amino-3-(3-hydroxy-5-methylisoxazol-4-yl)propionic acid (AMPA) in a sample of tissue obtained from the subject. In yet another embodiment, one or more neurological disorders can be screened for in a subject by determining the presence of β-N-oxalyl-amino-L-alanine (BOAA, also described as S-(−)-β-N-oxalyl-,β-diaminopropionic acid) in a sample of tissue obtained from the subject. It is understood that methods for determining of neurotoxic amino acid or neurotoxic derivative thereof include, when necessary, methods for distinguishing the neurotoxic isomer from the nonneurotoxic isomer of the same compounds, e.g., for distinguishing neurotoxic L-BOAA from non-neurotoxic D-BOAA.

Neurotoxic amino acids of the present invention can be non-protein amino acids including but not limited to, β-alanine (3-alanine), 4-aminobutyrate (GABA), 3-cyanoalanine (β-cyanoalanine), 2-aminobutyric acid, 2-methylene-4-aminobutyric acid, 3-methylene-4-aminobutyric acid, 2-aminoisobutyric acid, 5-aminolevulinic acid, 2-amino-4-methylhexanoic acid (homoisoleucine), 2-amino-4-methylhex-4-enoic acid, 2-amino-4-methylhex-5-ynoic acid, 2-amino-3-methylpentanoic acid, 2-aminoadipic acid, 4-ethylideneglutamic acid, 3-aminoglutaric acid, 2-aminopimelic acid, N4-ethylasparagine, N4-methylasparagine, erythro-4-methylglutamic acid, 4-methyleneglutamic acid, 4-methyleneglutamine, N5-methylglutamine, N5-ethylglutamine (theanine), N5-isopropylglutamine, 2-amino-4-(aminoxy)butyric acid (canaline), 2,4-diaminobutyrate, N4-acetyl-2,4-diaminobutyrate, N4-lactyl-2,4-diaminobutyrate, N4-oxalyl-2,4-diaminobutyrate, 2,3-diaminopropionic acid, N3-acetyl-2,3-diaminopropionic acid, N3-methyl-2,3-diaminopropionic acid, N3-oxalyl-2,3-diaminopropionic acid, N6-acetyllysine, N6-methyllysine, N6-trimethyllysine (laminine), ornithine (2,5-diaminopentanoic acid), saccharopine (N6-(2'-glutamyl)lysine, 2,6-diaminopimelic acid, N4-(2-hydroxyethyl)asparagine, erythro-3-hydroxyaspartic acid, 4-hydroxyarginine, 4-hydroxycitrulline, threo-4-hydroxyglutamic acid, 3,4-dihydroxyglutamic acid, 3-hydroxy-4-methylglutamic acid, 3-hydroxy-4-methyleneglutamic acid, 4-hydroxy-4-methylglutamic acid, 4-hydroxyglutamine, N5-(2-hydroxyethyl)glutamine, 5-hydroxynorleucine, threo-4-hydroxyhomoarginine, homoserine, O-acetylhomoserine, O-oxalylhomoserine, O-phosphohomoserine, 4-hydroxyisoleucine, 5-hydroxymethylhomocysteine, threo-3-hydroxyleucine, 5-hydroxyleucine, 2-hydroxylysine, 4-hydroxylysine, 5-hydroxylysine, N6-acetyl-5-hydroxylysine, N6-trimethyl-5-hydroxylysine, 4-hydroxyornithine, mimosine, 4-hydroxynorvaline, 5-hydroxynorvaline, 2-amino-4,5-dihydroxypentanoic acid, 2-amino-4-hydroxypimelic acid, 4-hydroxyvaline, O-acetylserine, O-phosphoserine, pipecolic acid (piperidine-2-carboxylic acid), 3-hydroxypipecolic acid, trans-4-hydroxypipecolic acid, trans-5-hydroxypipecolic acid, 5-hydroxy-6-methylpipecolic acid, 4,5-dihydroxypipecolic acid, trans-3-hydroxyproline, trans-4-hydroxyproline, trans-4-hydroxymethylproline, azetidine-2-carboxylic acid, N-(3-amino-3-carboxypropyl)azetidine-2-carboxylic acid, 4,5-dehydropipecolic acid (baikiain), 3-amino-3-carboxypyrrolidone (cucurbitine), 2-(cyclopent-2'-enyl)glycine, 5-hydroxytryptophan, albizziine (2-amino-3-ureidopropionic acid), arginosuccinic acid, canavinosuccinic acid, citrulline, homoarginine, homocitrulline, indospicine, O-ureidohomoserine, 6-hydroxykynurenine, 3-(4-aminophenyl)alanine, 3-(3-aminomethylphenyl)alanine, 3-(3-carboxyphenyl)alanine, 3-carboxytyrosine, 3-(3-hydroxymethylphenyl)alanine, 3-(3-hydroxyphenyl)alanine, 3-(3,4-dihydroxyphenyl)alanine (L-DOPA), 2-(phenyl)glycine, 2-(3-carboxyphenyl)glycine, 2-(3-carboxy-4-hydroxyphenyl)glycine, 2-(3-hydroxyphenyl)glycine, 2-(3,5-dihydroxyphenyl)glycine, 4-aminopipecolic acid, guvacine, 2-amino-4-(isoxazolin-5-one)-2-yl)butyric acid, lathyrine, or tetrahydrolathyrine. (Spencer and Berman, 2003, in, *Plant Toxins and Human Health*, CABI, pp 1-23). The present disclosure provides sufficient guidance for one of skill in the art to identify a neurotoxic non-protein amino acid of the present invention.

Neurotoxic derivatives of non-protein amino acids include but are not limited to metabolites, carbamate adducts, analogs, and other amino acid derivatives having neurotoxic activity. In accordance with one aspect, neurotoxic derivatives are carbamate adducts (carbamates) of neurotoxic amino acids. In one embodiment, neurotoxic derivatives of the present invention are carbamate adducts of BMAA, including α-N-carboxy-β-N-methylamino-L-alanine (BMAA-α-$NCO_2$) and/or β-(N-carboxy-N-methyl)-amino-L-alanine (BMAA-β-$NCO_2$), (Brownson et al., 2002, *J Ethnopharmacol* 82: 159-167; Myers and Nelson, 1990, *J Biol Chem* 265:10193-10195). In accordance with another aspect, neurotoxic derivatives include the neurotoxic isomer of a neurotoxic amino acid, although it could alternately be understood that the neurotoxic isomer is the neurotoxic amino acid in a particular embodiment. Neurotoxic derivatives may also be methylated, carbamoylated, or hydroxylated metabolites, or metabolites conjugated to sugars, lipids, or proteins. It is understood that the methods provided herein are suitable for determining neurotoxins associated with neurological disorders, and may provide a robust measurement of neurotoxin even when the compound being measured is not necessarily the compound or compounds acting in vivo in a particular subject. In one embodiment, the present disclosure provides methods for determining BMAA levels in tissue samples and environmental samples, and these methods generate robust results even when these methods do not distinguish whether BMAA, or a derivative such as a carbamate adduct of BMAA (e.g., (BMAA-α-$NCO_2$ or β-(N-carboxy-N-methyl)-amino-L-alanine (BMAA-β-$NCO_2$) is the most active compound in a particular embodiment. The methods presented herein are robust, and can be further refined by one of skill in the art, according to the particular circumstances of a particular embodiment.

In accordance with another aspect, the present invention provides methods for screening environmental samples for neurotoxic amino acids or neurotoxic derivatives thereof associated with neurological disorders. Screening environmental samples for neurotoxic amino acids or neurotoxic derivatives thereof includes, but is not limited to, screening to determine actual or potential exposure of a subject to neurotoxic amino acids or neurotoxic derivatives thereof associated with neurological disorders, and screening to identify environmental samples contaminated with neurotoxic amino acids or neurotoxic derivatives thereof associated with neurological disorders. In one embodiment, the present invention provides methods for determining BMAA levels in environmental samples including water samples or food items.

In accordance with yet another aspect, the present invention provides methods for inhibiting neurological disorders in a subject by reducing levels of a neurotoxic amino acid or neurotoxic derivative thereof associated with neurological disorders, e.g., by draining endogenous reservoirs of the neurotoxic amino acid or neurotoxic derivative thereof. Inhibiting includes, but is not limited to, treating existing neurological disorders or preventing neurological disorders. In one embodiment, the present invention provides methods for draining endogenous reservoirs of BMAA or derivatives thereof in a subject.

In accordance with another aspect, the invention provides methods for inhibiting a neurological disorder in a subject by interfering with the interaction between a neurotoxic amino acid or neurotoxic derivative thereof and its target molecule. In particular, the invention provides methods for inhibiting a neurological disorder by increasing the cellular concentration of a neuroprotectant compound that blocks interaction of a neurotoxic amino acid or neurotoxic derivative thereof with a target molecule. In one embodiment, the neurotoxic amino acid or neurotoxic derivative thereof is BMAA or a BMAA derivative, and the neuroprotectant compound is glutamic acid or a glutamic acid analog. Agents that bind neurotoxic amino acids or neurotoxic derivatives thereof can be included to sequester neurotoxic amino acid or neurotoxic derivative thereof released from endogenous reservoirs. Chelating agents can be included to chelate metal ions released when neurotoxic amino acids or neurotoxic derivatives thereof are released from endogenous reservoirs.

As provided herein, a subject may be any organism suitable for practicing the methods of the present invention. In particular, a subject is a mammal, more particularly a primate, even more particularly a human. In one embodiment, a subject is an experimental animal that is exposed to a neurotoxic amino acid or neurotoxic derivative thereof associated with neurological disorders. Such experimental animals include, but are not limited to, a mouse, rabbit, rat, bat, pig, sheep, cow, monkey, ape, or other animal suitable for research on neurological disorders. In one embodiment, methods of the present invention are carried out using an experimental animal for which an animal model of one or more neurological diseases exists. In another embodiment, methods of the present invention are carried out using an experimental animal as part of developing an animal model of one or more neurological diseases. In yet another embodiment, methods of the present invention are carried out using an experimental animal in which the effects of exposure to a neurotoxic amino acid or neurotoxic derivative thereof associated with neurological disorders are measured by studies of brain chemistry, structure, or function. In one embodiment, a subject is a human. In another embodiment, a subject is a human suffering from one or more neurological disorders. In another embodiment, a subject is a human who is asymptomatic for one or more neurological disorders. In another embodiment, a subject is a human who has been identified as being at risk for developing a neurological disorder. In yet another embodiment a subject is a human who is known or suspected of having been exposed to at least one neurotoxic amino acid or neurotoxic derivative thereof associated with neurological disorders.

In accordance with one aspect of the present invention, methods are provided for analyzing tissue samples from a subject, or environmental samples used in environmental screening, for one or more forms of neurotoxic amino acids or neurotoxic derivatives thereof associated with neurological disorders. Methods include analysis of free (e.g., unbound, cytosolic, circulating) forms of neurotoxic amino acids or neurotoxic derivatives thereof associated with neurological disorders, protein-bound forms of neurotoxic amino acids or neurotoxic derivatives thereof associated with neurological disorders (e.g., bound to proteins or incorporated into proteins), or conjugated forms of neurotoxic amino acids or neurotoxic derivatives thereof associated with neurological disorders (e.g., conjugated to sugars or lipids). One of skill in the art can determine what forms of neurotoxic amino acid or neurotoxic derivative thereof are present in a sample, and can further determine which forms are of diagnostic or predictive interest for a given embodiment. In one embodiment, tissue samples are analyzed for one or more forms of BMAA. BMAA can exist in a free (unbound) form in a tissue, or can exist in a protein-bound form, where it may be incorporated into a protein or it may be otherwise associated with a protein. In one embodiment, both free and protein-bound BMAA levels are determined. In another embodiment, only free BMAA levels are determined. In another embodiment, only levels of protein-bound BMAA are determined.

In accordance with another aspect, methods of the invention can be practiced using any tissue sample obtained from a subject, provided the tissue sample can be analyzed to determine the presence of a neurotoxic amino acid or neurotoxic derivative thereof associated with a neurological disorder. In one embodiment, a tissue sample may be analyzed to determine the presence of BMAA and if BMAA is present, to determine the amount of BMAA. Amounts of free BMAA and/or protein-bound BMAA may be quantified, according to the nature of the tissue sample and the question to be answered in a particular embodiment. In some embodiments, it may be desirable to determine both free and protein-bound BMAA levels. In other embodiments, it may be desirable to determine only free BMAA levels. In other embodiments, it may be desirable to determine only protein-bound BMAA levels. Tissue samples may be obtained from a living subject, or may be obtained from a preserved specimen, including stored tissue, biopsy and/or autopsy samples, or museum specimens. Stored tissue may be frozen tissue, histological specimens, tissue dried on solid storage media, or other forms of stored tissue. Suitable tissue samples include but are not limited to neurological tissue or non-neurological tissue. Neurological tissue can be associated with the central nervous system (CNS), including brain tissue or cerebral-spinal fluid (CSF), or may be associated with the peripheral nervous system (PNS). Non-neurological tissue can be keratinous tissue including but not limited to, hair, skin, nail, including fingernail or toenail, feather, claw, hoof, or horn. Non-neurological tissue can be non-keratinous tissue including but not limited to, bood, serum, saliva, or urine. In one embodiment, hair samples are analyzed to determine the level of protein-bound BMAA. In another embodiment, skin is analyzed to determine BMAA levels. In one embodiment, skin is analyzed to determine free BMAA levels and protein-bound BMAA. In another embodiment, skin is analyzed to determine only free BMAA levels. In another embodiment, skin is analyzed to determine only protein-bound BMAA levels. In yet another embodiment brain tissue is analyzed to determine BMAA levels. In yet another embodiment, samples of cerebrospinal fluid (CSF) are analyzed to determine the BMAA levels. Brain or CSF tissue may be analyzed to determine the levels of protein-bound BMAA, free BMAA, or both protein-bound and free BMAA, wherein protein-bound BMAA may be bound to neuroproteins or to other proteins.

Screening for Neurological Disorders

The present invention provides screening methods for neurological disorders. As provided herein, neurological disorders (also known as neurologic disorders, or neurologic diseases, or neurological diseases) are disorders that involve the central nervous system (brain, brainstem and cerebellum), the peripheral nervous system (including cranial nerves), and the autonomic nervous system (parts of which are located in both central and peripheral nervous system). It is understood that neurological disorders may have complex etiologies, such that one or more environmental or genetic factors may contribute to development of a neurological disorder in a subject. Neurological disorders include well-characterized disorders or syndromes such as Alzheimer's disease or Parkinson's disease, or may be signs (e.g., aphasia) or symptoms (e.g., tremors) that are observed in multiple disorders. It is further understood that the development of a neurological disorder in a subject may be due to one factor or a combination of factors. Likewise, it is understood that a particular neurological disorder in a subject may be due to different factors or different combinations of factors that resulted in the same neurological disorder in other subjects. Screening methods as provided herein are suitable for screening for neurological disorders wherein one or more environmental or genetic factor may play a part.

Screening methods include but are not limited to, methods for diagnosing one or more neurological disorders in a subject, methods for predicting the likelihood of developing one or more neurological disorders in a subject, methods for predicting the severity of a neurological disorder in a subject, and methods for determining exposure of a subject to neurotoxic amino acids or neurotoxic derivatives thereof associated with developing neurological disorders. Methods of the present invention include methods for carrying out repeated testing to generate time series data on the presence and levels of neurotoxic amino acids or neurotoxic derivatives thereof in a subject, and/or the presence and levels of neurotoxic amino acids or neurotoxic derivatives thereof in environmental samples.

In accordance with one aspect, methods are provided for diagnosing one or more neurological disorders in a subject. Methods include correlating the presence or absence of a neurotoxic amino acid or neurotoxic derivative thereof in tissue samples from a subject, with other physical or psychological determinations relevant to assessing neurological disorders. Methods further include correlating the levels of a neurotoxic amino acid or neurotoxic derivative thereof measured in one or more tissue samples from a subject, with other physical or psychological determinations relevant to assessing neurological disorders. In one embodiment, tissue samples are obtained from a subject diagnosed as having a neurological disorder, BMAA levels are determined, and these results are compared with other physical or psychological measurements of the subject, as part of a method for diagnosing one or more neurological disorders. Methods of invention can likewise be practiced to refine or confirm a diagnosis of one or more neurological disorders, or to exclude other possible diagnoses.

In one embodiment, tissue samples are obtained from a subject suspected of having a neurological disorder, BMAA levels are determined, and these results are compared with other physical or psychological measurements of the subject, as part of a method for diagnosing one or more neurological disorders. As disclosed in the Example 4 and Table 3 below, elevated levels of BMAA were found in brain tissue of six Chamorros suffering from ALS-PDC (lytico-bodig) at the time of their death. As further disclosed in Example 4, elevated levels of BMAA were also found in brain tissue of Canadian patients diagnosed as suffering from Alzheimer's Disease (AD) at the time of death.

In yet another embodiment, BMAA levels are measured in tissue samples from a subject who is currently asymptomatic for one or more neurological disorders. As disclosed in Example 4 and Table 3 below, elevated levels of BMAA were found in brain tissue of a Chamorro patient who was asymptomatic for ALS-PDC at the time of death. In a further embodiment, BMAA levels are measured in tissue samples from a subject who is currently asymptomatic for one or more neurological disorders, as part of a method for identifying subjects at risk of developing a neurological disorder, who may be in need of additional monitoring.

In accordance with another aspect, methods are provided for determining the severity of one or more neurological disorders in a subject. Without wishing to be limited by this theory, one indicator of the severity of a neurological disorder is the level of a neurotoxic amino acid or neurotoxic derivative thereof measured in a tissue sample from a subject. In one embodiment, the BMAA levels are measured in a tissue sample from a subject diagnosed as having, or suspected of having, one or more neurological disorders, where higher BMAA levels are correlate with a more severe neurological disorder.

In accordance with another aspect, methods are provided for predicting the likelihood of developing a neurological disease. Methods include correlating the levels of a neurotoxic amino acid or neurotoxic derivative thereof measured in one or more tissue samples, with other physical or psychological determinations relevant to assessing neurological disorders. Methods of the present invention further include correlating the levels of a neurotoxic amino acid or neurotoxic derivative thereof measured in one or more tissue samples from a subject, with genetic analysis of the subject to determine the likelihood of developing a neurological disease. Genetic analysis includes analysis of family history and/or genotyping tissue samples, as part of a method for determining the likelihood of developing a neurological disease. Without wishing to be limited by this theory, the likelihood of a subject developing a neurological disorder shows a direct correlation with the presence of neurotoxic amino acid or neurotoxic derivative thereof measured in a tissue sample from a subject. As disclosed in the Example 4 below, elevated levels of BMAA were found in brain tissue of six Chamorros suffering from ALS-PDC (lytico-bodig). As further disclosed in Example 4, elevated levels of BMAA were also found in brain tissue of individuals who died from Alzheimer's Disease. Accordingly, in one embodiment, BMAA levels are determined in tissue samples from subjects having symptoms of one or more neurological disorders. In another embodiment, BMAA levels are determined in tissue samples from subjects asymptomatic for neurological disorders.

In accordance with another aspect, methods are provided for predicting the severity of a neurological disease in a subject considered to be at risk for developing one or more neurological disorders. Without wishing to be limited by this theory, levels of BMAA in a tissue sample from a subject are understood to correlate directly with the severity of a neurological disorder once it develops in the subject. Methods of the invention therefore include correlating the levels of a neurotoxic amino acid or neurotoxic derivative thereof measured in one or more tissue samples, with other physical or psychological determinations relevant to predicting the severity of a neurological disorder. Methods of the present invention further include correlating the levels of a neurotoxic amino acid or neurotoxic derivative thereof measured in one or more tissue samples from a subject, with genetic analysis of the subject, to predict the severity of a neurological disease in a subject considered likely to develop one or more neurological disorders. Genetic analysis includes analysis of family history and/or genotyping tissue samples.

In accordance with another aspect, methods are provided for longitudinal studies of neurological disorders by taking tissue samples at repeated intervals over a period of time and BMAA levels are determined in each tissue sample, providing time series data on BMAA levels useful for longitudinal studies. BMAA levels were measured over time in a subject suffering from progressive supranuclear palsy (PSP). In yet another embodiment, BMAA levels in tissue samples from a subject are repeatedly measured over a period of time, in order to determine the level of BMAA release over time, providing data useful for predicting the likelihood and/or timing and/or severity of future onset of one or more neurological disorders.

The invention provides methods for screening neurological disorders including but not limited to, Parkinson's disease (PD), Alzheimer's disease (AD), progressive supranuclear palsy (PSP), amyotropic lateral sclerosis (ALS), and the neuropathological disease known as ALS-PDC (or, lytico-bodig disease). The teachings of the present disclosure provide sufficient guidance to identify other neurological disorders for which the present invention provides screening methods: one of skill in the art can practice the methods of the present invention to determine the levels of a neurotoxic amino acid or neurotoxic derivative thereof in tissue samples from a subject, then compare these levels with other indicia of neurological disease in the subject, and ascertain whether a correlation exists between levels of the neurotoxic amino acid or neurotoxic derivative thereof, and indicia of a particular neurological disease.

In accordance with one aspect, methods as provided herein are suitable for screening for neurodegenerative disorders with neurofibrillary tangles (known as neurofibrillary tangle disorders or NFT disorders), including but not limited to argyrophilic grain disease, Alzheimer's disease, ALS-PDC of Guam, corticobasal degeneration, mytonic dystrophy, Pick's disease, postencephalitic parkinsonism, primary progressive aphasia, progressive supranuclear palsy (PSP), and subacute sclerosis panencephalitis. These disorders are generally characterized by neurofibrillary degeneration (NFD) leading to intraneuronal accumulation of pathological tau proteins into abnormal filaments and sometimes called "tauopathies." Different NFT disorders have distinct tau pathologies (that is, tau protein isoforms and distribution in brain). In accordance with one aspect of the invention, levels of a neurotoxic amino acid or neurotoxic derivative thereof, e.g., BMAA, are measured in a tissue sample from a subject known or suspected to be suffering from an NFT disorder. In accordance with another aspect, levels of neurotoxic amino acid or neurotoxic derivative thereof, e.g., BMAA, are measured in a tissue sample from a subject who is asymptomatic for an NFT disorder. In accordance with another aspect, levels of modified acids, e.g., BMAA, are measured in a tissue sample from a subject who is asymptomatic for an NFT disorder but is considered to be at risk for developing an NFT disorder, e.g, based a family history of NFT disorders, or based on known or suspected exposure to environmental factors associated with NFT disorders. Analysis of brain tissue according to the methods of the present invention permits comparison of BMAA levels with other factors including, but not limited to, identifying whether NFTs are present, identifying which tau protein isoforms are present, and investigating the distribution pattern of tau protein and/or NFTs in the brain of the subject.

In one embodiment, BMAA levels are measured in brain tissue of a subject known or suspected to be suffering from ALS-PDC, which has a distinct tau pathology from other NFT disorders. In another embodiment, BMAA levels are measured in brain tissue of a subject known or suspected to be suffering from Alzheimer's disease, which has a distinct tau pathology from other NFT disorders. In another embodiment, BMAA levels are measured in brain tissue of a subject known or suspected to be suffering from progressive supranuclear palsy (PSP) and/or corticobasal degeneration, which have a distinct tau pathology from other NFT disorders. In another embodiment, BMAA levels are measured in brain tissue of a subject known or suspected to be suffering from Pick's disease, which has a distinct tau pathology from other NFT disorders. In another embodiment, BMAA levels are measured in brain tissue of a subject known or suspected to be suffering from myotonic dystrophy, which has a distinct tau pathology from other NFT.

In one embodiment, BMAA levels in tissue samples from subjects diagnosed as suffering from Alzheimer's disease are determined according the methods of the present invention. In another embodiment, BMAA levels are determined in tissue samples from subjects who are asymptomatic for Alzheimer's disease. In yet another embodiment, BMAA levels in tissue samples from subjects who are asymptomatic for Alzheimer's, but are suspected to be at risk of developing Alzheimer's disease, are determined according to the methods of the present invention.

In accordance with another aspect, methods as provided herein are useful for distinguishing between neurological disorders and/or screening individuals having a neurological disorder for additional neurological disorders. In one embodiment, an individual with Down's syndrome, a neurological disorder caused by trisomy of chromosome 21 and characterized by symptoms including NFTs, is screened for neurotoxic amino acid or neurotoxic derivative thereof as provided herein. In one embodiment, detecting the presence of BMAA in a subject suffering from Down's syndrome can be used to identify a subject at risk of developing a neurological disorder associated with a neurotoxic amino acid or neurotoxic derivative thereof. In another embodiment, detecting the presence of BMAA in a subject suffering from Down's syndrome can be used to distinguish between multiple neurological disorders in a subject. In another embodiment, detecting the presence of BMAA in a subject suffering from Down's syndrome can be used to distinguish between possible causes (etiologies) of a sign or symptom of a neurological disorder.

In accordance with another aspect, methods as provided herein are useful for screening for dementias including but not limited to Alzheimer's disease (AD), Lewy body dementia (LBD, also called dementia with Lewy bodies (DLB)) and vascular dementia. In accordance with another aspect, methods as provided herein are useful for screening for movement disorders including but not limited to Parkinson's disease (PD), dystonias (sustained involuntary muscle contractions), Huntington's disease (Huntington's chorea), multiple system atrophy, progressive supranuclear palsy, corticobasal degeneration, dyskinesias, essential tremor, hereditary spastic paraplegia, myoclonus, restless legs syndrome, Rett syndrome, spasticity, Sydenham's chorea, Tourette's syndrome, and Wilson's disease. In accordance with another aspect, methods as provided herein are useful for screening for motor neuron diseases (MND) including but not limited to amyotrophic lateral sclerosis (ALS), progressive muscular atrophy (muscular dystrophy (MD)), and postpolio syndrome. In accordance with yet another aspect, methods as provided herein are useful for screening for amyotrophic lateral sclerosis/parkinsonism-dementia complex of Guam (ALS/PDC, also known as lytico-bodig).

It is understood that methods as provided herein are suitable for screening for neurological disorders regardless of whether any signs or symptoms of neurological disorders are present. As disclosed in the Example 4 below, elevated levels of BMAA were found in brain tissue from one Chamorro who was asymptomatic for ALS-PCD, while another asymptomatic Chamorro did not have detectable BMAA levels. This result is consistent with the observation that neurofibrillary tangles have been observed in brain tissue of certain Chamorros who did not show symptoms of ALS-PDC.

It is further understood that methods as provided herein are suitable for screening for neurological disorders regardless of whether a particular neurological disorder can be diagnosed. Because distinct disorders often share similar signs and symptoms (e.g., tremors, dementia, aphasia), methods of the present invention may be suitable as part of an initial screening for neurological disease, wherein the results of the initial screening are relied upon for determining what further tests are needed for a thorough assessment. For example, subjects with ALS-PDC can have symptoms similar to Alzheimer's disease or Parkinson's disease, or both diseases, and although ALS-PDC is considered a separate disorder, it is also possible for a subject with ALS-PDC to also suffer from Alzheimer's disease or Parkinson's disease. Accordingly, measurement of BMAA levels in a subject may aid in identifying which neurological disorders are present are contributing to the signs and symptoms observed in the subject.

Neurological disorders include, but are not limited to: acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease (AD); amyotrophic lateral sclerosis (ALS); amyotrophic lateral sclerosis/parkinsonism-dementia complex of Guam (ALS/PDC); anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; Batten disease; Behcet's disease; Bell's palsy; benign essential blepharospasm; benign focal amyotrophy; benign intracranial hypertension; Binswanger's disease; blepharospasm; Bloch-Sulzberger syndrome; brachial plexus injury; brain abscess; brain injury; brain tumor; spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; Chiari malformation; chorea; chronic inflammatory demyelinating polyneuropathy (CIDP); chronic pain, chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; Herpes zoster oticus; Herpes zoster; Hirayama syndrome; holoprosencephaly; Huntington's disease; hydranencephaly; hydrocephalus; hypercortisolism; hypoxia; immune-mediated encephalomyelitis; inclusion body myositis; incontinentia pigmenti; infantile phytanic acid storage disease; infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (ALS); lumbar disc disease; Lyme disease, neurological sequelae; Lytico-Bodig syndrome (ALS-PCD); Machado-Joseph disease; macrencephaly; megalencephaly; Melkersson-Rosenthal syndrome; Menieres disease, meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; Moyamoya disease; mucopolysaccharidoses; multi-infarct dementia; multifocal motor neuropathy; multiple sclerosis; multiple system atrophy with postural hypotension; muscular dystrophy; myasthenia gravis; myelinoclastic diffuse sclerosis; myoclonic encephalopathy of infants; myoclonus; myopathy; myotonia congenita; narcolepsy; neurofibromatosis; neuroleptic malignant syndrome; neurological manifestations of AIDS; neurological sequelae of lupus; neurological sequelae of Lyme disease; neuromyotonia; neuronal ceroid lipofuscinosis; neuronal migration disorders; Niemann-Pick disease; O'Sullivan-McLeod syndrome, occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease (PD); paramyotonia congenita; paraneoplastic diseases; paroxysmal attacks; Parry Romberg syndrome; Pelizaeus-Merzbacher disease; periodic paralyses; peripheral neuropathy; persistent vegetative state; pervasive developmental disorders; photic sneeze reflex; phytanic acid storage disease; Pick's disease; pinched nerve; pituitary tumors; polymyositis; porencephaly; post-polio syndrome; postherpetic neuralgia; postinfectious encephalomyelitis; postural hypotension; Prader-Willi syndrome; primary lateral sclerosis; prion diseases; progressive hemifacial atrophy; progressive multifocal leukoencephalopathy; progressive sclerosing poliodystrophy; progressive supranuclear palsy (PSP); pseudotumor cerebri; Ramsay-Hunt syndrome; Ramsay Hunt syndrome Type I; Ramsay Hunt syndrome Type II; Rasmussen's Encephalitis; reflex sympathetic dystrophy syndrome; Refsum disease—infantile; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shingles; Shy-Drager syndrome; Sjogren's syndrome; Soto's syndrome; spasticity; spina bifida; spinal cord injury; spinal cord tumors; spinal muscular atrophy; Stiff-Person syndrome; stroke; Sturge-Weber syndrome; subacute sclerosing panencephalitis; subcortical arteriosclerotic encephalopathy; Sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette's syndrome; transient ischemic attack; transmissible spongiform encephalopathies; transverse myelitis; traumatic brain injury; tremor; trigeminal neuralgia; tropical spastic paraparesis; tuberous sclerosis; vasculitis including temporal arteritis; Von Hippel-Lindau Disease (VHL); Wallenberg's syndrome; Werdnig-Hoffman disease; West syndrome; Williams syndrome; Wilson's disease; Zellweger syndrome.

Screening for Environmental Factors Associated with Neurological Disorders.

In accordance with one aspect, methods are provided for screening for environmental factors associated with neurological disorders. Environmental factors associated with neurological disorders include, but are not limited to, a neurotoxic amino acid or neurotoxic derivative thereof, e.g., BMAA. Screening as provided herein includes, but is not limited to, testing environmental samples to determine actual or potential exposure of a subject to a neurotoxic amino acid or neurotoxic derivative thereof associated with neurological disorders. An environmental sample may be obtained from material that is ingested, e.g. a water sample or a food sample. An environmental sample may be material that is deliberately ingested, e.g., water used for drinking, or plants or animals that are part of the food supply or food chain. Alternately, an environmental sample may be obtained from material that is incidentally ingested, e.g., material from an organism whose contents or secretions become associated with other ingested material, such as cyanobacterial symbionts present in plants used for food, or cyanobacteria in water used for washing or drinking.

In one embodiment, the BMAA levels in environmental samples are measured to determine the actual or potential exposure of a subject to BMAA. Measurements of BMAA levels in environmental samples leads to a determination of potential or actual exposure to BMAA, and these measurements can be used to predict the likelihood that neurological disorders will develop in a subject exposed to these environmental samples. It is understood that BMAA in cycad tissues and other plant tissues, is produced by cyanobacterial symbionts and taken up by the cycads and other organisms that feed on cycads (Example 3). Numerous samples from an archive of cyanobacteria have been tested for the ability to produce BMAA, and nearly all strains tested produce BMAA. In light of the discovery of symbiotic cyanobacteria as the source of BMAA in cycads (Example 3), coupled with the near ubiquity of cyanobacteria in soil and water, and the discovery that many cyanobacterial strains produce BMAA, it is proposed that BMAA may be present in many environments. Accordingly, methods of the present invention may further include screening environmental samples for the presence of cyanobacteria in addition to screening for particular factors such as BMAA.

In accordance with another aspect, an environmental sample is water known to contain cyanobacteria. In another embodiment, an environmental sample is water suspected of containing cyanobacteria. In another embodiment, an environmental sample is water whose contents are unknown. In another embodiment, an environmental sample may be an food animal that ingests cyanobacteria-containing water, e.g., a fish, bird, deer, or domesticated animal. In another embodiment, an environmental sample may be lichen or moss or liverworts that contain or live in symbiosis with cyanobacteria.

In another embodiment, an environmental sample may be a marine or freshwater alga or a marine or freshwater fungus that contain or live in symbiosis with cyanobacteria. In another embodiment, an environmental sample may be a marine or freshwater invertbrate that contains or lives in symbiosis with cyanobacteria. In another embodiment, an environmental sample may be a stromatolite, or a petrochemical deposit, or a mineral deposit left by cyanobacteria. In another embodiment, an environmental sample may be a food animal that ingests a plant, lichen, moss, alga, marine invertebrate, that contain cyanobacteria or a stromatolite, petrochemical deposit, or mineral deposit left by cyanobacteria, e.g. a reindeer, caribou, deer, moose, marine or freshwater fish, bird, reptile, or domesticated animal.

In accordance with another aspect, an environmental sample is screened to determine if the sample is associated with a neurological disorder, by detecting the presence of cyanobacteria that produce a neurotoxic amino acid or neurotoxic derivative thereof, in the environmental sample. By screening environmental samples to detect cyanobacteria that product neurotoxic amino acids or neurotoxic derivatives thereof, it is possible to determine actual or potential exposure of a subject to environmental factors associated with a neurological disorder. Neurotoxic amino acids or neurotoxic derivatives thereof, e.g., BMAA, have been found in many cyanobacteria strains of genera including, but not limited to, *Nostoc* and *Anabena*.

In accordance with another aspect, a plurality of environmental samples is tested to determine the levels of neurotoxic amino acids or neurotoxic derivatives thereof associated with neurological disorders, at different levels throughout a food chain. Without wishing to be limited by this theory, biomagnification of factors associated with neurological disorders, e.g., BMAA, can occur by accumulation of a factor in tissues of organisms at different trophic levels, with the result that consumption of an organism from a higher trophic level may give a much higher exposure to a neurotoxin than consumption of an organism from a lower trophic level. In one embodiment, a plurality of environmental samples is tested in a food chain, including cycad coralloid roots, cycad leaves, cycad seeds, and tissue samples from flying foxes (bats) known to eat cycad seeds. In another embodiment, a plurality of environmental samples is tested in a food chain, including water, aquatic plants, food animals that ingest the water or aquatic plants, e.g., fish birds, a wild or domesticated animal, and carnivores that ingest plant-eating animals. In one embodiment, a plurality of environmental samples can be tested to determine whether a factor such as BMAA is found in a particular food chain. After testing a plurality of environmental samples, levels of a neurotoxic amino acid or neurotoxic derivative thereof can be compared and analyzed for evidence of accumulation or biomagnification in the food chain.

In accordance with a further aspect, a tissue sample from a subject is also tested, in addition to testing environmental samples for a neurotoxic amino acid or neurotoxic derivative thereof associated with neurological diseases. This provides methods for determining accumulation or biomagnification of environmental factors (neurotoxic amino acids or neurotoxic derivatives thereof) in a food chain and correlating levels of these environmental factors in each step of the food chain with the frequency or severity of neurological disorders in subjects that consume material from various trophic levels of the food chain. In one embodiment, a tissue sample from a subject with symptoms of, or a diagnosis of, a neurological disorder is tested for a neurotoxic amino acid or neurotoxic derivative thereof associated with neurological diseases. In another embodiment, a tissue sample from a subject asymptomatic for a neurological disorder is tested for a neurotoxic amino acid or neurotoxic derivative thereof associated with neurological diseases. This aspect of the present invention provides a powerful tool for linking neurological disorders with exposure to environmental factors that are known or suspected to be associated with neurological disorders. As shown in Example 4 below, elevated BMAA levels were detected in brain tissues of subjects who died of ALS-PDC after known exposure to food sources that were known or suspected to contain BMAA—that is, the subjects who died of ALS-PDC were Chamorros who had eaten a traditional Chamorro diet at some time in their life. Without wishing to be limited by this theory, these results are congruent with the results presented in Example 2 below, showing high concentrations of BMAA in specimens of flying foxes, a traditional Chamorro food, leading to the prediction by the inventors that consumption of a single flying fox would result in a dose of BMAA equivalent to the dose obtained by eating 174-1,014 kg of processed cycad flour. In addition, elevated BMAA levels were detected in one Chamorro subject who was asymptomatic for ALS-PDC and died of other causes. Without wishing to be limited by this theory, it should be noted that this result is congruent with the report by Forman et al. on a study of 30 Chamorros (Forman et al., 2002, *Am J Pathol* 160: 1725-1731), which found neurofibrillary tangles in brain tissue of both affected (ALS-PDC) and unaffected (asymptomatic) Chamorros. In contrast, another Chamorro subject who was asymptomatic for ALS-PDC and died of other causes, did not have detectable BMAA levels in brain tissue.

Another aspect of the invention provides methods for detecting environmental contamination by environmental factors associated with neurological disorders. Surprisingly, elevated BMAA levels were found in brain tissue of non-Chamorro (Canadian) subjects who had suffered from Alzheimers disease (see, Examples below) and in a non-Chamorro (Canadian) suffering from progressive supranuclear palsy (PSP). In accordance with this aspect of the invention, elevated BMAA in brain tissue of these Alzheimer's disease patients, and the elevated BMAA in tissue samples from a PSP patient, indicated that these subjects had been exposed to environmental sources of BMAA at some time in their life. These results suggested that bioaccumulation of cyanobacterial BMAA may occur through different food chains in other areas. Since the frequency of illness in a population exposed to neurotoxins is a function of dose, even low levels of progressive neurological disorders might be related to exposure to low concentrations of BMAA in water supplies contaminated by cyanobacteria. Accordingly, environmental screening as provided herein can be carried out to investigate possible environmental sources of BMAA or other environmental factors associated with neurological disorders. Environmental screening as provided herein can be carried out to prevent or minimize exposure of other subjects to BMAA or other environmental factors associated with neurological disorders, thereby decreasing the risk of developing a neurological disorder associated with BMAA or other factors.

In accordance with a further aspect, the present invention can be used to protect subjects from exposure to environmental factors associated with neurological disorders by developing assays and assay kits for such factors. In one embodiment, assays are provided to test food samples, including plant or animal matter, for BMAA. In another embodiment, assays are provided to test water supplies for BMAA. In yet another embodiment, assays kits are provided for environmental screening for BMAA, where kits include materials for practicing methods of the invention to test water supplies, food supplies, and other environmental samples, to protect subjects from exposure to BMAA. In accordance with another aspect, assays and assay kits for BMAA can be used for public health purposes, e.g., to indicate contamination of a water supply or food source with cyanobacteria that produce BMAA.

Reservoirs of Neurotoxic Amino Acids or Neurotoxic Derivatives Thereof Associated with Neurological Disorders Neurotoxic amino acids or neurotoxic derivatives thereof may accumulate in one or more endogenous reservoirs in a subject. BMAA is of natural origin, unlike certain other environmental factors associated with neurological disorders, e.g., mercury or PCBs. Protein-bound BMAA has been found in various tissues, suggesting possible incorporation during protein synthesis or through association with a carrier protein. Earlier reports indicated that 90% of injected BMAA is not eliminated from either urine or feces in rats, suggesting that BMAA accumulates in subjects, particularly in mammals. These findings, in combination with the epidemiological observation of a period of latency associated with ALS-PDC, suggest an endogenous neurotoxic reservoir from which BMAA may be released over time, probably as a result of protein metabolism. Without wishing to be bound by this theory, the BMAA reservoir may function as a "slow toxin" causing damage in a subject through at least five different possible neuropathological routes: (1) incorporation of non-protein amino acids such as BMAA may alter tertiary folding of neuroproteins, altering their biological activity; (2) protein-associated BMAA may form dimers that covalently bind metal ions, which could result in a protein punctuated with reactive non-protein amino acid complexes that alter ionic balance in neuronal cells, generate free radicals, or even catalyze deleterious chemical processes; (3) capture and release of metal ions such as those of $Zn^{2+}$, $Cu^{2+}$, or $Ca^{2+}$ by BMAA complexes may interfere with the proper function of NMDA and AMPA receptors; (4) BMAA incorporation may truncate proteins before completed synthesis or collapse proteins after release from the ribosome, where such truncation of protein synthesis is characteristic of many of the tauopathies (NFT disorders); and (5) BMAA may be slowly released in free form through protein metabolism in the brain, serving as an agonist at AMPA, NMDA, and other neuroreceptors. The latter activity may effectively translate a single ingestion, or episodic ingestions, of BMAA into a highly prolonged, constant low level exposure of BMAA within the superior frontal gyrus, possibly resulting in neuron death via excitotoxicity. Etiologically, such prolonged low-level exposure may not produce acute disease, such as has been observed in animal models, but instead might result in both the latency and progressive nature typified by ALS-PDC among the Chamorro people. Protein-associated BMAA in endogenous reservoirs may therefore be the hypothesized "slow toxin" of ALS-PDC.

A study was carried out to determine whether BMAA is associated with proteins in the food chain. As shown in the Examples below, protein-bound BMAA was measured by removing all free amino acids from samples of cyanobacteria, cycad seed tissue, flying fox (bat) hair and skin, and human brain tissue. After all free amino acids were removed, the protein fraction was hydrolyzed. The hydrolyzed proteins were then tested for BMAA. Protein-bound BMAA was found in all tissues tested. Without wishing to be limited by this theory, this finding of protein-bound BMAA in all tissues suggests possible incorporation during protein synthesis, or through association with a carrier protein.

The results disclosed herein indicate that BMAA, which originates with cyanobacteria, accumulates in plant and animal tissues that become part of the food chain. In particular, these results shows that BMAA of cyanobacterial original accumulates in the Guam food chain, where it is biomagnified by flying foxes who consume BMAA-containing cycad seeds and accumulate BMAA, and may be further biomagnified when Chamorro people eat flying foxes containing large amounts of BMAA, with the result that BMAA accumulation in brain tissue is associated with the ALS-PDC neurological disorder among the Chamorro people.

The brain tissue in which BMAA was detected exhibited intercellular neurofibrillary tangles, extracellular neurofibrillary tangles and cell loss. In one Lytico-Bodig (ALS-PDC) patient, no unbound BMAA was found in the brain tissue, but more than 1 mg/g BMAA was recovered from the protein-bound fraction. In all other patients, there was roughly a 60-130 fold greater quantity of protein-bound BMAA compared to the BMAA recovered from the free amino acid pool (free BMAA). This suggests that the rate of amino acid flux between the protein-bound BMAA and free BMAA, varies between individuals, and may be subject to nutritional status, genetic proclivities, age, endocrine function, or idiopathic differences. Without wishing to be limited by this theory, protein-bound BMAA represents the BMAA reservoir for a subject, and may be the more robust indicator in screening for neurological disorders. The relative amounts of BMAA in the protein-bound form (e.g., in the "endogenous neurotoxic reservoir") and in the unbound form in the free amino acid pool should be compared with clinical manifestations of neurological disorders, to determine the dose/duration relationship.

The possibility of alternative pathways for bioaccumulation of cyanobacterial BMAA in other parts of the world is supported by the finding of protein-associated BMAA in brain tissue of Alzheimer's patients from Canada. As shown in Table 3, high levels of protein-bound BMAA (149-1190 µg/g) were found in frontal cortex tissue of all six Chamorrow patients who had died from ALS-PDC. Frontal cortex tissue from five of six Chamorro patients who had died from ALS-PDC also had high levels of free BMAA (3-10 µg/g). In addition, significant amounts of free and protein-bound BMAA was found in one asymptomatic Chamorro patient who did not die of ALS-PDC, consistent with previous findings of Chamorros who exhibited no clinical manifestations of ALS-PCD, but who showed significant neuroanatomical pathologies when autopsied. Significant concentrations of BMAA were found in the frontal gyrus of brain cortex of two Canadian patients who were diagnosed as suffering from Alzheimer's disease at the time of their death. In the same study, brain tissue of thirteen Canadian patients who did not have a diagnosis of Alzheimer's disease and died of other causes, did not have detectable levels of BMAA. The unexpected finding of BMAA in Canadian patients suffering from Alzheimer's disease, which is a disorder with a tau pathology distinct from that of ALS-PDC, suggests that BMAA is present and may accumulate in other food chains, finally accumulating in human subjects in a reservoir from which BMAA may be released over time. Since there was no indication that the Canadian Alzheimer's patients ever lived in Guam or consumed a Chamorro diet, the MDAA found in their brains must ultimately be traced to a non-cycad source. Accordingly, the present invention provides methods for determining exposure and biomagnification of environmental factors associated with neurological disorders, including methods for identifying the vectors of biomagnification.

Inhibiting Neurological Disorders: Treatment and/or Prevention

In accordance with yet another aspect, the present invention provides methods for inhibiting neurological disorders in a subject. In accordance with one aspect, neurological disorders are inhibited by reducing levels of a neurotoxic amino acid or neurotoxic derivative thereof associated with neurological disorders. In accordance with another aspect, neurological disorders are inhibited by reducing the toxic effect of a neurotoxic amino acid or neurotoxic derivative thereof associated with neurological disorders. In accordance with one aspect, neurological disorders are inhibited by interfering with the interaction of a neurotoxic amino acid or neurotoxic derivative thereof with target molecules. It is understood that neurological disorders can be inhibited by treating one or more existing disorders, or by treating early symptoms or signs of disorders, or by preventing the onset of one or more disorders, or by preventing the progression (worsening) of one or more disorders.

In accordance with one aspect, levels of a neurotoxic amino acid or neurotoxic derivative thereof can be reduced by releasing the neurotoxic amino acid or neurotoxic derivative thereof from an endogenous reservoir in the subject. The invention further provides methods for minimizing damage from releasing a neurotoxic amino acid or neurotoxic derivative thereof from endogenous reservoirs including, but not limited to, providing neuroprotectant compounds that interfere with the interaction of the neurotoxic amino acid or neurotoxic derivative thereof with a target molecule, or providing compounds to bind and inactivate the neurotoxic amino acid or neurotoxic derivative. In one embodiment, a neurological disorder can be inhibited by releasing ("draining") BMAA from endogenous reservoirs, to prevent accumulation in a subject. In one embodiment, a subject is infused with a monoclonal antibody against BMAA when BMAA is released from the reservoir. In another embodiment, the subject is infused with glutamate as a neuroprotectant compound when BMAA is released from the reservoir. In a further embodiment, a subject is infused with metal chelating compounds to absorb metal ions released when BMAA is released from the reservoir.

In accordance with another aspect, the toxic effects of a neurotoxic amino acid or neurotoxic derivative thereof associated with a neurological disorder are reduced by adding neuroprotectant compounds that interfere with the interaction of the neurotoxic amino acid or neurotoxic derivative thereof with target molecules, thereby diluting the effective level of the neurotoxic amino acid or neurotoxic derivative thereof. In one embodiment, the toxic effects of BMAA are reduced by increasing the intracellular levels of glutamic acid (possibly ionized as glutamate) or glutamic acid homologs, such that the effective pool of BMAA is diluted and target molecules are protected. In this embodiment, glutamic acid or glutamate functions as a neuroprotectant compound. In a further embodiment, chelating agents are added.

Kits for Screening for Neurotoxic Amino Acids or their Derivatives

The present invention further provides kits for screening a subject having or at risk of having a neurological disorder, wherein the kits include a means for obtaining a tissue sample from the subject and a means for analyzing the tissue sample to determine the presence of a neurotoxic amino acid or neurotoxic derivative thereof associated with the neurological disorder. Means for obtaining tissue samples are known in the art. Means for analysing a tissue sample to determine the presence of a neurotoxic amino acid or neurotoxic derivative thereof are known in the art; non-limiting embodiments are disclosed herein. The kit may include means for determining the presence of a glutamate receptor agonist such as a methylated alanine, in particular BMAA. The kit may include means for analyzing protein-bound BMAA, free BMAA, or both protein-bound BMAA and free BMAA in the sample. In accordance with one aspect, kits of the present invention include "control" samples of one or more neurotoxic amino acids being determined, to facilitate both detection and quantification of each neurotoxic amino acid or neurotoxic derivative thereof being determined in the sample. In one embodiment, a kit includes thin layer chromatography (TLC) plates, such that tissue samples and control samples can be spotted on plates, separated by solvent migration, and determined.

In accordance with one aspect of the invention, a kit may include means for analyzing a plurality of tissue samples from the subject. In one embodiment, the tissue samples may include a sample of a tissue in which a neurotoxic amino acid or neurotoxic derivative thereof is known to accumulate and a sample of a tissue in which neurotoxic amino acid or neurotoxic derivative thereof is known to not accumulate, thereby permitting a determination of whether neurotoxic amino acids have accumulated in certain tissues. In another embodiment, the tissue samples may include a sample of at least two distinct tissues in which a neurotoxic amino acid or neurotoxic derivative thereof is known to accumulate, permitting a determination of the relative levels of accumulation in different tissues. In accordance with another aspect of the invention, a kit may include means for performing repeated screening of the subject. In one embodiment, the subject is screened at repeated intervals that may stretch over days, months, or years. Kits of the present invention can be used in longitudinal studies as described above.

EXAMPLES

Example 1

Distribution of BMAA in *Cycas micronesica* Hill

The concentrations of BMAA and glutamic acid (GLU) were measured in different cycad tissues. Other known nitrogenous neurotoxins, including the carbamate precursors DAB, DAP, and ODAP (also known as BOAA) were also measured.

BMAA, GLU, DAB, DAP, and ODAP (BOAA) were measured in wild seeds of *Cycas micronesica* Hill collected from Guam, and in various tissues from living specimens of *Cycas micronesica* Hill of known provenance in the Fairchild Tropical Gardens, the Montgomery Botanical Center, and the National Tropical Botanical Garden. Herbarium tissue from the National Tropical Botanical Garden was also analyzed, as BMAA has been found to be stable in dried mammal specimens of great age (Banack & Cox, 2003).

BMAA and GLU were quantified from free amino acid extracts of cycad tissues following the techniques of Kisby, Roy & Spencer (1988) with minor modifications. Aqueous or trichloroacetic acid sample extracts were derivatized with 6-aminoquinolyl-N-hydrozysuccinimidyl carbamate (ACQ) following standardized protocols (Cohen & Michaud, 1993). Free amino acids were separated by reverse phase separation on a gradient HPLC system (Waters 717 Automated Injector, Waters 1525 Binary Solvent Delivery System and Waters Nova-Pak C18 column, 300 mm×3.9 mm) at 37° C. Individual compounds were eluted from the column with a gradient elution of 140 mM sodium acetate, 5.6 mM triethylamine, pH 5.2 and 60% acetonitrile (Cohen & Michaud, 1993). The identities of the BMAA peak and the GLU peak were confirmed by comparison to authenticated standards and were re-verified by modified gradient elution. The concentration of BMAA and GLU in samples was determined by fluorescence detection (Waters 2487 Dual-1 Fluorescence Detector) with excitation at 250 nm and emission at 395 nm with concurrent UV detection (Waters 2488 UV detector) at 254 nm. Detection of the ACQ-derivatized BMAA was dependent on concentration and comparison of equal amounts of BMAA and a norleucine internal standard resulting in a mean response of 51.2%. These data may be indicative of internal quenching of the derivative, but did not significantly affect sample quantification as the percentage response was consistent across the quantifiable concentration range. The limits of detection (LOD) and limits of quantification (LOQ) were determined by a concentration gradient of an authenticated standard (Sigma Chemical Co., St. Louis, Mo.). The LOD and the LOQ were 0.00013 µmoles and 0.013 µmoles respectively per injection for all analyses. As shown in Table 1 below, for purposes of data interpretation, all sample analyses were quantified within the range of the LOQ, or were reported as not present. Authenticated standards for DAB (2,4-diamino butyrate), DAP (2,3-diaminopropionate) and BOAA (β-N-oxalyl-amino-L-alanine) were also used to identify the corresponding HPLC peaks for presence or absence of these compounds, but no attempt was made to quantify their concentrations. Breeze scientific software (Trinity Consultants Inc., Dallas Tex.) was used to control system operation and collect and analyze data.

As shown in Table 1, BMAA and GLU occurred in various cycad tissues, as did compounds corresponding to the neurotoxins DAB, DAP, and BOAA. GLU was found in substantially higher quantities than BMAA in all tissues.

TABLE 1

BMAA and GLU concentrations (µg/g) in *Cycas micronesica* Hill tissues.

| Tissue | Sample size | BMAA mean (µg/g) | GLU mean (µg/g) | BOAA | DAP | DAB |
|---|---|---|---|---|---|---|
| root, non-coralloid | 3 | — | 45,922 | † | | |
| root, coralloid, non-infected | 2 | — | 86,900 | † | | |
| root, coralloid, mild infection | 2 | 37 | 9,449 | † | | |
| root, coralloid, heavy infection | 2 | 2 | 22,988 | † | † | |
| roots, coralloid, senescent infection | 1 | — | 6,435 | — | | |
| senescent stem, inner cortex | 3 | — | 22,781 | — | | |
| stem, outer cortex | 1 | — | 103,919 | — | | |
| stem, xylem | 3 | — | 18,323 | — | | |
| Leaf | 3 | 13 | 65,953 | † | | † |
| leaf mucilage | 1 | — | — | — | | |
| male sporophyll, immature | 1 | 663 | 57,334 | — | | |
| male sporophyll, mature | 1 | — | 57,819 | — | | |
| male sporangia, immature | 2 | 1546 | 68,202 | † | | |
| male sporangia, mature | 2 | 11 | — | † | † | † |
| female sporophyll | 2 | — | — | — | | † |
| seed sarcotesta | 3 | 9 | — | — | — | — |
| seed sarcotesta, outer integument layer | 3 | 1161 | — | † | — | — |
| seed gametophyte | 3 | 240 | 35,700 | † | — | — |

Samples were analyzed by HPLC and compared with amino acid standards.
Legend:
† = trace amounts
— = not detectable For purposes of comparison, the relative concentrations of BMAA and GLU were normalized by dividing the concentration for each molecule by the maximum concentration found (FIG. 1). The highest concentrations of BMAA were found in plant reproductive tissues. Concentrations of GLU were similar in all tissues tested, and showed no clear pattern of distribution. Although GLU appeared to be distributed throughout the plant without any apparent pattern, BMAA was concentrated in the male and female reproductive tissue where it may act as a deterrent to herbivory. The high concentration of BMAA in the outer layer of the sarcotesta showed that any animal that forages on cycad sarcotesta (e.g., flying foxes) would be exposed to high cumulative doses of BMAA over time. Other neurotoxic compounds were detected but not quantified in various parts of the cycad tissues including BOAA, DAB, DAP (Table 1).

Example 2

Biomagnification of Cycad Neurotoxins in Flying Foxes (Bats) of Guam

BMAA levels were measured in tissues of *Cycas micronesica* Hill from Guam, and tissues of *Pteropus mariannus mariannus*, an indigenous flying fox (bat) of Guam. Because *Pteropus mariannus mariannus* is now highly endangered, BMAA levels were measured in skin tissue from museum specimens of three flying foxes that were collected five decades ago in Guam, preserved as dried study skins, and deposited at the Museum of Vertebrate Zoology (MVZ), at the University of California, Berkeley.

Seeds of *Cycas micronesica* Hill collected from Guam, and samples of processed (washed, detoxified) cycad flour specimens collected from Guam (Dr. J. C. Steele, 1987-1988) were analyzed for their BMAA content. Traditional preparation of cycad flour by the Chamorros commonly involves soaking the gametophytes of the seeds of *Cycas micronesia* Hill for about 3 weeks with changes of water every 2-3 days.

BMAA was detected using high performance liquid chromatography (HPLC), and results were confirmed with thin layer chromatography (TLC) and gas chromatography-mass spectroscopy (GC-MS). For BMAA analysis, free amino acid extracts of flying fox and cycad tissues were prepared. Tissue samples were rehydrated for 30 minutes with water or trichloroacetic acid (mean tissue prep 80 mg/ml±32 SD), macerated, and filtered. Extracts were derivatized with 6-aminoquinolyl-N-hydrozysuccinimidyl carbamate (ACQ) following standardized protocols. Free amino acids were separated by reverse phase separation on a gradient HPLC system (Waters 717 Automated Injector, Waters 1525 Binary Solvent Delivery System and Waters Nova-Pak C18 column, 300 mm×3.9 mm) at 37° C. Individual compounds were eluted from the column with a gradient elution of 140 mM sodium acetate, 5.6 mM triethylamine, pH 5.2 (mobile phase A) and 60% acetonitrile (mobile phase B) with a flow rate of 1.0 ml/min.9 Gradient conditions were as follows: initial=100% A, 2.0 min=90% A curve 11, 5.0 min=86% A curve 11, 10.0 min=86% A curve 6, 18.0 min=73% A curve 6, 30.0 min=60% A curve 10, 35.0 min=40% A curve 6, 39.0 min=10% A curve 6, followed by a wash with 100% B for 5 minutes and reequilibration for 5 minutes at 100% A. BMAA peak identity was confirmed by comparison to a commercial standard (Sigma B-107; >94% pure) and was re-verified by modified gradient elution. The concentration of BMAA in samples was determined by the fluorescent tag using a Waters 2487 Dual-1 Fluorescence Detector, with excitation at 250 nm and emission at 395 nm. Detection of the ACQ-derivatized BMAA was dependent on concentration and quantification was accomplished with comparison of equal amounts of BMAA and a norleucine internal standard (representing a single mid-range concentration) resulting in a mean response of 51.2%. These data expressed the average response of values for several experiments and depict the efficiency of the derivatization protocol and the relative ratio between BMAA and the internal standard. The results may have been indicative of internal quenching of the derivativized compound, but did not significantly affect sample quantification as the percentage response was consistent across the quantifiable concentration range. The limits of detection (LOD, defined as the lowest concentration of an analyte in a sample that can be detected though not necessarily quantitated) and limits of quantification (LOQ, the concentration within the linear range of the calibration curve relating absorbance to concentration) were determined by a concentration gradient of an authenticated standard (Sigma Chemical Co., St. Louis, Mo.). The LOD was 0.00013 µmoles per injection and LOQ was 0.013 µmoles per injection for all analyses. For data interpretations, all sample analyses were quantified within the range of the LOQ or were reported as not detected (ND) (Table 1). Breeze scientific software (Trinity Consultants Inc., Dallas Tex.) was used to control system operation and collect and analyze data.

To confirm the identity of BMAA in HPLC fractions, TLC was carried out using HPLC fractions and BMAA standards (BMAA, Sigma B-107; Methionine, Aldrich 15, 169-6). Briefly, 0.5 min HPLC fractions of derivatized standards and tissue samples were collected and pooled, and then were concentrated in a Savant speed-vac concentrator and spotted on channels of TLC plates. TLC was carried out using glass-backed 250 µm analytical layer silica gel plates (20×20 cm) with a mobile phase of 60 ml butanol:15 ml glacial acetic acid:25 ml 0.5 N NaCl. After drying, the BMAA on plates were visualized with a 365 nm ultra-violet light. Finally, GC-MS of HPLC fractions containing peaks identified as BMAA confirmed the presence of BMAA at 02.1 m/z for both the Sigma Standard compound and a sample isolated from flying fox (bat) tissue (MVZ 114607).

TABLE 2

BMAA in samples of cycads, cycad flour, and flying foxes

| Species | Sample | Concentration (µg/g) | Based on Kisby et al. 1992 | Based on Duncan et al. 1990 | Current calculation |
|---|---|---|---|---|---|
| *Cycas micronesica* | Gametophyte | 240 | | | |
| | Sarcotesta | 9 | | | |
| | outer integument of sarcotesta | 2,657 | | | |
| | | | Concentration (µg/g)* | | |
| Cycad seed flour | Merizo village | 3 | 18 | 73 | |
| | Agat village | 8 | 1 | 4 | |
| | Yigo village | ND | 5 | 8 | |

TABLE 2-continued

BMAA in samples of cycads, cycad flour, and flying foxes

| Species | Sample | Concentration (µg/g) | Based on Kisby et al. 1992 | Based on Duncan et al. 1990 | Current calculation |
|---|---|---|---|---|---|
| | | | Equivalent mean dose in kg of cycad flour | | |
| Pteropus | 114607 | 7,502 | 690 | 104 | 1,014 |
| mariannus | 114606 | 1,879 | 173 | 26 | 254 |
| (dried skin) | 114609 | 1,287 | 118 | 18 | 174 |

*Mean concentration reported, based on published values with reported sample sizes ranging from 1 to 4, found in Kisby et al., 1992, Neurology, 42: 1336:1340 and Duncan et al., 1990, Neurology 40: 767-772.

As shown in Table 2, flying fox skin tissue contained elevated quantities of BMAA (1,287 to 7,502 µg/g), in contrast to the sarcotesta of cycad seeds which had a mean BMAA concentration of 9 µg/g. However, the outermost integument of the seed had extraordinarily high concentrations of BMAA up to 2,657 µg/g. These results showing the abundance of BMAA in the fifty-year old museum specimens of flying fox (bat) tissues, demonstrated that the Chamorro people who consumed this once-abundant flying fox species unwittingly ingested high doses of BMAA. For example, consumption of MVZ flying fox specimen #114607, assuming a fresh weight of 500 g and uniform distribution of BMAA throughout the specimen, resulted in the ingestion of 3,751 mg of BMAA, which is comparable to consuming 1,014 kg of processed cycad flour. Table 2 further shows comparative values of BMAA concentrations in cycad flour samples from published reports. Differences in the values in Table 2 reflect different extraction methods, differences in the analytic methodology, and values that were not adjusted for efficiency of BMAA recovery.

Example 3

Cyanobacterial Neurotoxins: Cyanobacterial Origin of BMAA

BMAA was quantified in 200 mg samples of actively growing cyanobacteria isolated from infected coralloid roots of *Cycas micronesia* Hill, cycad tissues; *Azolla* plants (collected near Hanapepe, Kauai); *Gunnera* plants (collected from Mt. Wailaleale, Kauai). All samples were homogenized twice in 0.1 N trichloroacetic acid and centrifuged at 15,800×g for 3 min to precipitate proteins and extract free amino acids. Protein-bound BMAA was released by hydrolysis of the precipitate in 6N HCl under nitrogen for 24 hours, followed by centrifugation and ultrafiltration to remove sediment. An aliquot of the hydrolysis extract was then freeze-dried to complete dryness and resuspended in 20 mM HCl for derivatization. Sample extracts were derivatized with 6-aminoquinolyl-N-hydroxysuccinimidyl carbamate and amino acids quantified via HPLC separation as described above.

The presence of BMAA in the samples, as well as the identity and purity of the BMAA peak in the HPLC fractions, was verified by liquid chromatography mass spectroscopy (LC-MS) using an Agilent 1100 HPLC coupled with a variable wavelength diode array detector (DAD) and an SL single quadrapole MS with an atmospheric pressure ionization source (API) using the electrospray ionization interface (ESI). Compounds were separated on a Waters Symetry-Shield RP 18 column heated at 30° C. with a linear gradient elution of CH3CN (10 40%) in water. Nitrogen gas was purified and supplied to the ESI interface with a nebulizing pressure of 35 psi and two distinct modes were used for detection of compounds within the MS. The DAD detected compounds at 254 nm with a full spectral scan from 200 600 nm and 0.5 nm resolution within a semi micro flow cell. The initial signal was determined in positive scan mode with a 100 600 Da range at 50V fragmentor voltage, at a gain of 1.0 V. BMAA was identified through selective ion monitoring (SIM) in the positive ion mode with a dwell time of 45 msec and a 70 V fragmentor voltage. For both signals, the capillary voltage was 4 kV and the electron multiplier voltage gain was 4 V. The cycle time was 0.82 sec/cycle, split 50% for each of the two MS signals.

Cyanobacterial Origin of BMAA

Cyanobacterial symbionts were isolated from infected coralloid roots of *Cycas micronesica* Hill, harvested from three accessioned specimens (vouchered specimens of known provenance) growing in the National Tropical Botanical Garden, Kalaheo, Kauai, and grown as an axenic culture with repeated passages. For analysis of cycad root tissues infected with cyanobacterial symbionts, soil-borne bacteria were removed from root tissues of *Cycas micronesica* Hill by surface-sterilizing roots immersion in a solution of 70% ethanol for 3 min, followed by a 30 min immersion in 1.6% sodium hypochlorite with 2 drops of surfactant and 3 sequential washes with sterile deionized water. Surface-sterilized root explants (1-2 cm long) were excised and cultured onto standard BG-11 medium, pH 7.1 solidified with gellam gum (Sigma). Root explant cultures were incubated in a controlled environment room with a 16 h photoperiod at a light intensity of 35-45 µmole/m$^2$/s and temperatures of 25-30° C. After 7-10 days of culture, proliferation of colonies of the cyanobacterial symbiont of the root explants was clearly visible. Serial subculture of individual cyanobacterial colonies ensured the absence of residual BMAA from root tissue. To assess the effects of amino acids on cyanobacterial growth, BG-11 medium was supplemented with glutamate or glutamine (0, 126, or 250 µmol/L); cyanobacterial growth was increased two-fold by supplementation with these amino acids. Histological verification of culture purity was conducted prior to chemical analyses. The cyanobacterial colonies appeared to be generally devoid of heterocysts, and prolific filamentous growth was observed.

Results. BMAA was not detected in non-infected cycad roots, but was abundant in coralloid roots infected by the cyanobacterial symbiont *Nostoc*, where coralloid roots with mild infections had 37 µg/g BMAA and coralloid roots with heavy infections had 2 µg/g BMAA. Axenic cultures of *Nostoc* isolated from coralloid roots were found to have 0.3 µg/g of BMAA. In non-root cycad tissues, BMAA is concentrated in cycad seeds (which are eaten by flying foxes), with 9 μg/g BMAA in the fleshy sarcotesta, and up to 2,657 μg/g BMAA in the outer integument layer of the sarcotesta. See also, results in Table 1.

Additional studies of two unrelated plant species with cyanobacterial symbionts were carried out to determine that cyanobacterial symbionts were a source of BMAA in plant hosts. *Azolla filiculoides*, a floating fern in rice paddies with a cyanobacterial symbiont, had 2 μg/g of BMAA. *Gunnera kauaiensis*, a large-leafed angiosperm with a cyanobacterial symbiont, had 4 μg/g of BMAA in petiolar tissue. Levels of BMAA in the protein pellet (protein-bound BMAA) were about 240-fold higher than the level for BMAA quantified as free amino acid. These results confirmed that BMAA of cyanobacterial origin may be found in many environments and may be ingested in many food chains.

Example 4

BMAA in Brain Tissues

BMAA levels were measured in 200 mg samples of the superior frontal gyrus of brains of eight (8) Chamorro patients in Guam, and fifteen (15) Canadian patients. Tissues were provided by Dr. Patrick McGeer of the University of British Columbia, Vancouver, B.C., Canada. Autopsied tissues from patients were fixed in paraformaldehyde prior to storage in 15% buffered sucrose maintenance solution, where the time interval between death and autopsy varied from 4 hours to 5 days. Familial relationships, clinical histories, and histochemical characteristics of the Chamorro patients had been disclosed previously (McGeer et al, 1997, *Neurology* 49, 400-409). In addition, autopsied tissued from Canadian patients was provided, including two samples from two (2) Canadian patients who were clinically diagnosed with Alzheimer's disease prior to death, and thirteen (13) Canadian patients who died of natural causes other than progressive neurodegenerative diseases.

Tissues were homogenized twice in 0.1 N trichloroacetic acid and centrifuged at 15,800×g for 3 min to precipitate proteins and extract free amino acids. Protein-bound BMAA was released by hydrolysis of the precipitate at 110° C. in constant boiling 6N HCl for 24 hours. Particulate matter was removed from a 500 μl aliquot by ultrafiltration (Ultrafree-MC, Millipore Corp.) at 15,800×g and the resulting extract was freeze-dried. Amino acids were resuspended in 20 mM HCl, applied to a Sep-Pac $C_{18}$ cartridge equilibrated with sequential washes of 100% methanol, 50% methanol in water, and a gradient of borate buffer:acetronitrile (0.5M borate:0-60% $CH_3CN$) at 20% increments. BMAA in sample extracts was derivatized with 6-aminoquinolyl-N-hydroxysuccinimidyl carbamate following standardized protocols (Banack et al., 2003, *Neurology* 61: 387-389). Amino acids were quantified via HPLC separation as described above (Example 3). The presence of BMAA in the samples, as well as the identity and purity of the BMAA peak in the HPLC fractions, was verified by liquid chromatography mass spectroscopy (LC-MS) using an Agilent 1100 HPLC coupled with a variable wavelength diode array detector (DAD) and an SL single quadrapole MS with an atmospheric pressure ionization source (API) using the electrospray ionization interface (ESI). Compounds were separated on a Waters SymetryShield RP 18 column heated at 30° C. with a linear gradient elution of CH3CN (10 40%) in water. Nitrogen gas was purified and supplied to the ESI interface with a nebulizing pressure of 35 psi and two distinct modes were used for detection of compounds within the MS. The DAD detected compounds at 254 nm with a full spectral scan from 200 600 nm and 0.5 nm resolution within a semi micro flow cell. The initial signal was determined in positive scan mode with a 100 600 Da range at 50V fragmentor voltage. BMAA was identified using the extracted ion chromatogram in which the molecular ion peak was confirmed.

Results. As shown in Table 3, high levels of protein-bound BMAA (149-1190 μg/g) were found in frontal cortex tissue of all six Chamorrow patients who had died from ALS-PDC. Frontal cortex tissue from five of six Chamorro patients who had died from ALS-PDC also had high levels of free BMAA (3-10 μg/g). In addition, significant amounts of free and protein-bound BMAA was found in one asymptomatic Chamorro patient who did not die of ALS-PDC, consistent with previous findings of Chamorros who exhibited no clinical manifestations of ALS-PCD, but who showed significant neuroanatomical pathologies when autopsied. Significant concentrations of BMAA were found in the frontal gyrus of brain cortex of two Canadian patients who were diagnosed as having died from Alzheimer's disease. Frontal cortex tissues of the other thirteen Canadian patients, all of whom died of other causes, did not have detectable levels of BMAA.

TABLE 3

Quantification of free and protein-associated BMAA in superior frontal gyrus tissue of Chamorro and Canadian patients

| Clinical Diagnosis at Death | Nationality | Age at Death | Gender | Free BMAA (μg/g) | Protein-bound BMAA (μg/g) |
| --- | --- | --- | --- | --- | --- |
| PDC (Lytico-bodig) | Chamorro | 60 | M | ND | 1190 |
| PDC (Lytico-bodig) | Chamorro | 69 | M | 6.7 | 644 |
| ALS (Lytico-bodig) | Chamorro | 68 | F | 10.1 | 610 |
| PDC (Lytico-bodig) | Chamorro | 77 | M | 7.0 | 736 |
| PDC (Lytico-bodig) | Chamorro | 60 | M | 9.1 | 149 |
| PDC (Lytico-bodig) | Chamorro | 67 | F | 3.3 | 433 |
| Asymptomatic | Chamorro | 41 | M | 4.8 | 82 |
| Asymptomatic | Chamorro | 61 | M | ND | ND |
| Alzheimer's | Canadian | — | — | 3.4 | 220 |
| Alzheimer's | Canadian | — | — | 9.7 | 264 |
| Metastic cancer | Canadian | 39 | F | ND | ND |
| Heart failure | Canadian | 62 | M | ND | ND |
| Cancer of the esophagus | Canadian | 69 | M | ND | ND |
| Chronic obstructive pulmonary disease | Canadian | 80 | M | ND | ND |

TABLE 3-continued

Quantification of free and protein-associated BMAA in superior frontal gyrus tissue of Chamorro and Canadian patients

| Clinical Diagnosis at Death | Nationality | Age at Death | Gender | Free BMAA (μg/g) | Protein-bound BMAA (μg/g) |
|---|---|---|---|---|---|
| Lymphoma | Canadian | 60 | F | ND | ND |
| Cancer of the thyroid | Canadian | 86 | F | ND | ND |
| Heart failure | Canadian | 89 | M | ND | ND |
| Cancer of the pancreas | Canadian | 76 | M | ND | ND |
| Chronic obstructive pulmonary disease | Canadian | 89 | M | ND | ND |
| Heart failure | Canadian | 71 | F | ND | ND |
| Acute heart attack | Canadian | 80 | F | ND | ND |
| Chronic heart failure | Canadian | 87 | F | ND | ND |
| Aortic aneurysm | Canadian | 85 | F | ND | ND |

Various modifications can be made to the preferred embodiments without departing from the spirit and scope of the invention as defined in the appended claims.

What is claimed is:

1. A method of screening a subject comprising analyzing a keratinous tissue sample from the subject to determine the presence of protein-bound β-N-methylamino-L-alanine (BMAA) or 2,4-diaminobutyrate.

2. The method of claim 1, wherein the tissue sample is analyzed for protein-bound BMAA.

3. The method of claim 1, wherein protein-bound 2,4-diaminobutyrate is analyzed.

4. The method of claim 1, further wherein free BMAA or 2,4-diaminobutyrate is analyzed.

5. The method of claim 1, wherein the keratinous tissue is selected from the group consisting of hair, skin, nail, fingernail, toenail, feather, claw, hoof and horn.

6. The method of claim 5, wherein the keratinous tissue is hair.

7. The method of claim 5, wherein the keratinous tissue is selected from the group consisting of nail, fingernail and toenail.

8. The method of claim 5, wherein the keratinous tissue is skin.

9. The method of claim 8, wherein the skin is a skin biopsy.

10. A method of screening a subject comprising analyzing a tissue sample from the subject to determine the presence of protein-bound β-N-methylamino-L-alanine (BMAA) or 2,4-diaminobutyrate, wherein the tissue is saliva or urine.

11. A method of screening a subject comprising analyzing a tissue sample from the subject to determine the presence of β-N-methylamino-L-alanine (BMAA) or 2,4-diaminobutyrate, wherein protein-bound BMAA or 2,4-diaminobutyrate is analyzed.

* * * * *